US00PP17183P2

(12) United States Plant Patent
Kordes

(10) Patent No.: US PP17,183 P2
(45) Date of Patent: Nov. 7, 2006

(54) MINIATURE ROSE PLANT NAMED 'KORPAGBEL'

(50) Latin Name: *Rosa hybrida*
Varietal Denomination: KORpagbel

(75) Inventor: Tim-Hermann Kordes, Offenseth-Sparrieshoop (DE)

(73) Assignee: W. Kordes Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 37 days.

(21) Appl. No.: 10/985,078

(22) Filed: Oct. 28, 2004

(51) Int. Cl.
*A01H 5/00* (2006.01)

(52) U.S. Cl. ..... Plt./120

(58) Field of Classification Search ..... Plt./120
See application file for complete search history.

(56) References Cited

PUBLICATIONS

Application for EU PBR, W. Kordes Söhne.

*Primary Examiner*—Anne Marie Grunberg
*Assistant Examiner*—Annette H Para

(57) ABSTRACT

A new and distinct variety of miniature rose with long lasting, novel pink flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida*, var. 'KORpagbel'.

BACKGROUND OF THE INVENTION

The new variety of miniature rose plant of the present invention originated from a controlled crossing in a breeding program between 'KORnisecco', a non-patented rose and 'KORanalafi' a non-patented rose.

The two parents were crossed and the resulting seeds were planted in a controlled greenhouse environment. The resulting seedlings exhibited distinctive physical and biological characteristics. The new rose plant was selected as a single plant from the seedling beds due to its superior characteristics for further evaluation. This new and distinctive miniature rose variety is named 'KORpagbel'.

SUMMARY OF THE INVENTION

The new rose plant may be distinguished from its seed parent, KORnisecco by the following combination of characteristics:

1. KORpagbel has light salmon-pink flowers while KORnisecco has cream colored flowers,
2. KORpagbel has very double flowers while KORnisecco has only double flowers; and
3. KORpagbel as a shelf life of 21 days while KORnisecco has a shelf life of only 14 days.

The new rose plant may be distinguished from its pollen parent, KORanalafi by the following combination of characteristics:

1. KORpagbel has light salmon-pink flowers while KORanalafi has salmon-orange flowers, 2. The flowers of KORpagbel have a diameter of 40–50 mm while the flowers of KORanalafi have diameters of 30 mm,
3. KORpagbel has a better branching while KORanalafi has fewer branches.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of qualities is not present in prior rose cultivars. These objectives have been substantially achieved and in that distinguish 'KORpagbel' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpagbel' was selected in May, 2001 from the seedling beds and asexually propagated for further evaluation. The first asexual reproduction of 'KORpagbel' by softwood cuttings was in July, 2001 at the Rosa-Danica Nursery in Odense, Denmark.

This initial and other subsequent propagations conducted in controlled environments show that the foregoing and all other characteristics of 'KORpagbel' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORpagbel'. Specifically illustrated in SHEET ONE.

DETAILED BOTANICAL DESCRIPTION

Figures 1, 2, 3, 4, 5, 6:
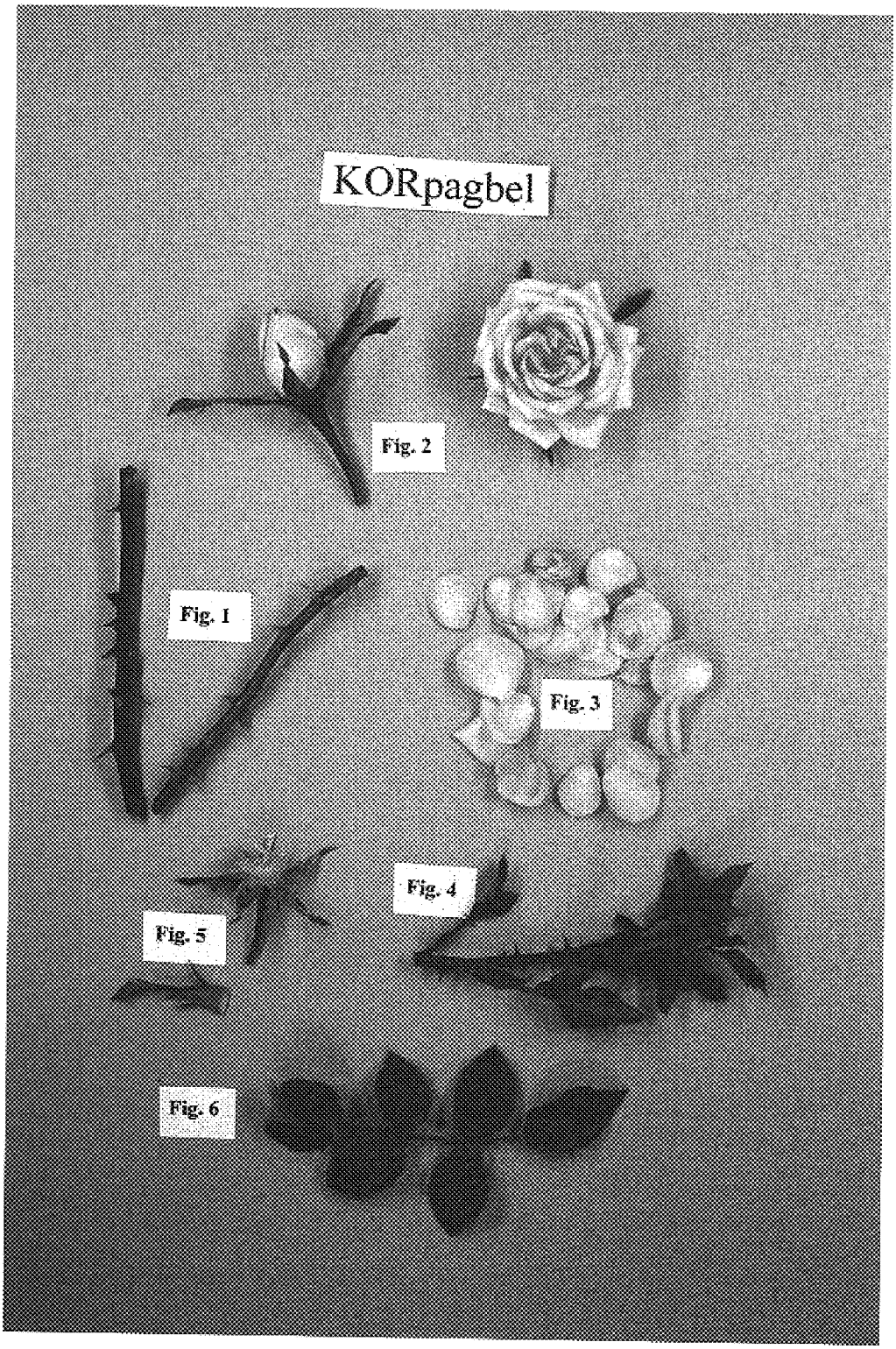
FIG. 1. Stem exhibiting thorns.
FIG. 2. Tight bud and half opened flower bloom.
FIG. 3. Flower petals, detached.
FIG. 4. Juvenile foliage and tip of stem.
FIG. 5. Receptacle and detached sepal.
FIG. 6. A single leave.

The following is a description of>KORpagbel, as observed in its growth in October, 2003 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORstrunek', a non-patented rose variety from the same inventor compared to 'KORpagbel' in Chart 1.

CHART 1

| | 'KORpagbel' | 'KORstrunek' |
|---|---|---|
| Flower petal, inner side. | Red Group 41D. | Red-Purple Group 70D |
| Flower petal, outer side. | Red Group 49B. | Red-Purple Group 62A |
| Flower petal, basal spot. | Yellow Group 2C | Green-White Group 157B |
| Flower bud shape. | High centered. | Broadly ovate. |

Parents:

*Seed parent.*—'KORnisecco'.

*Pollen parent.*—'KORanalafi'.

Classification:

*Botanical classification.*—*Rosa hybrida*, var. 'KORpagbel'.

*Commercial classification.*—Miniature rose.

FLOWER AND FLOWER BUD

Blooming habit: Recurrent.

*Flower bud.*—Size: Upon opening, 30–35 mm in length from base of receptacle to end of bud. Bud form: Long. Pointed ovoid to high centered. Bud color: As sepals first unfold, bud color is Red Group 36A. When ¼ open, the upper surface of petals is Red Group 36A and the lower surface is Red Group 36A. Sepals: Size: Average 25–40 mm long×6–8 mm wide. Shape: Strong foliaceous appendages on three of the five sepals. Sepal apex is cirrose. Base is flat at union with receptacle. Quantity: Five. Surface texture: Slight to moderate pubescence. Stipitate glands are present on margins of sepals with foliaceous appendages. Color: Upper surface Green Group 137A. Lower surface Green Group 138A.

*Receptacle.*—Surface: With numerous short fine white hairs. Color: Green Group 138A with intonations of Greyed-Green Group 182A. Shape: Funnel. Size: 6–8 mm (h)×8–10 mm (w).

*Peduncle.*—Surface: With numerous short fine white hairs and a few stipitate glands. Length: 30–40 mm average length. Diameter: 1.5–2.0 mm average diameter. Color: Green Group 138A with intonations of Greyed-Green Group 182A. Strength: Strong.

*Borne.*—Generally singly. Some stems with up to 2 buds per flowering stem.

Flower bloom:

*Fragrance.*—Light.

*Duration.*—Long lasting. A blooming plant with flowers has a commercial shelf life of 24 days. The blooms have a duration on the plant of approximately 16 to 18 days. As a cut flower, 10 to 12 days.

*Size.*—Large for a 10.5 cm pot rose. Average flower diameter is 40–50 mm when open.

*Form.*—Elegant long high-centered flower bud opens to a flattened convex when fully opened. Shape of flower when viewed from the side: Upon opening, upper part: Convex. Upon opening, lower part: Convex. Open flower, upper part: Flattened convex. Open flower, lower part: Flattened convex.

Color:

*Upon opening, petals.*—Outermost petals: Outer Side: Red Group 49B. Inner Side: Red Group 41D. Innermost petals: Outer Side: Red Group 49B. Inner Side: Red Group 41D.

*Upon opening, basal petal spots.*—Basal petal spot, outermost petals: Outer Side: Yellow Group 2C. Inner Side: Yellow Group 2C. Basal petal spot, innermost petals: Outer Side: Yellow Group 2C. Inner Side: Yellow Group 2C.

*After opening, petals.*—Outermost petals: Outer Side: Red Group 37C. Inner Side: Red Group 37D. Innermost petals: Outer Side: Red Group 37C. Inner Side: Red Group 37D.

*After opening, basal petal spots.*—Basal petal spot, outermost petals: Outer Side: Yellow Group 2D. Inner Side: Yellow Group 2D. Basal petal spot, innermost petals: Outer Side: Yellow Group 2D. Inner Side: Yellow Group 2D. Variegations: Some intonations of Yellow-Green Group 151D on outer surface of guard petals.

General tonality: On open flower Red Group 37C to Red Group 37D. No change in the general tonality at the end of the sixth day. Afterwards, general tonality is Red Group 36C.

Petals:

*Petal count.*—Very double. Approximately 40–45 petals under normal conditions.

*Petal reflex.*—Innermost petals reflex somewhat. Outermost petals double reflexed.

*Petal edge.*—Entire.

*Petal shape.*—Apex shape is round. Shape of base is round.

*Petal size.*—20–25 mm long; 18–25 mm wide.

*Thickness.*—Average.

*Petal arrangement.*—Generally in a regular pattern with overlapping edges.

*Petaloids.*—Present. Average of 8–10 per flower. Petaloids are 6–10 mm long and 6–8 mm wide. Color of inner side is Red Group 41C. Color of outer side is Red Group Red Group 41C. Surface texture is smooth. Shape is linear to elliptic.

Reproductive organs:

*Pistils.*—Approximately 85–90 present. Stigmas: Location: Slightly superior in location to anthers. Color:

Green-White Group 157B. Styles: Length: 5–7 mm long. Color: Green-White Group 157C with intonations of Red-Purple Group 64D.

*Stamens.*—Approximately 95–100 on average and regularly arranged around the styles. Anthers: Size: 1.5–2.0 mm long. Color: Yellow-Green Group 153D. Quantity: Approximately 91–95. Pollen: Scant. Color: Yellow-Green Group 151D. Filaments: Color: Yellow-Green Group 151D. Length: 6–8 mm.

THE PLANT

*Plant growth.*—Moderately vigorous. Upright to bushy. When grown as a 10.5 cm pot plant, the average height of the plant itself is 18–20 cm and the average width is 16–18 cm. When grown as a budded nursery plant the average plant height is 70–75 cm and the average plant width is 50–60 cm.

*Stems.*—The flowering stems on outdoor grown, budded plants are upright with multiple lateral side branches which terminate in flower buds. Canes are 5 mm in diameter. Stem color: Young wood: Green Group 138A. Older wood: Green Group 138A. Stem surface: Young wood: Smooth. Older wood: Smooth.

*Prickles.*—Present. Incidence: 8–10 per cm of stem. Decreasing in incidence on upper portion of flowering canes. Size: Average length: 6 mm. To 8 mm in length. On upper 25% of flowering stems thorns are smaller, averaging 4 mm, and needlelike. Color: Green Group 138A. Intonations of Greyed-Red Group 183D on most thorns. Shape: Deeply concave on lower portions of stems, linear on upper portions of stems.

*Leaves and leaflets.*—Normally 5 leaflets on normal leaves in middle of the stem. Leaf size: 70–100 mm (l)×50–60 mm (w). Shape: Pointed oval. Quantity: Average abundance. Texture: Matte on upper side. Color, mature foliage: Upper Leaf Surface: Green Group 137A. Lower Leaf Surface: Green Group 138A. Color, juvenile foliage: Upper Leaf Surface: Green Group 137A. Lower Leaf Surface: Green Group 138A. Anthocyanin intonation: Present. Color is Greyed-Purple Group 183D. Location: Intonations present on juvenile stems, thorns, petioles, stipules, rachis, leaflets and leaflet margins. Intonations also on mature wood of stems and thorns.

*Stipules.*—Size: 17 mm (l)–8 mm (w). Stipule color: Green Group 137A. Intonations of Greyed-Red Group 183D. Presence of stipitate glands: Present on margins. Margins: Serrated.

*Petiole.*—Length: 10–15 mm. Diameter: 1.5 mm average diameter. Petiole color: Green Group 137A. Underneath: With 1–2 small prickles. Anthocyanin: Present. Greyed-Green Group 183D. Prickles: Small, 1–1.5 mm. Stipitate glands: Present on margins of petiole.

*Petiole rachis.*—Color: Green Group 137A. Underneath: With limited numbers of fine white hairs and 1–2 small prickles. Anthocyanin: Present. Greyed-Green Group 183D. Prickles: Small. 1–1.5 mm. Stipitate glands: Present on margins.

*Leaflets.*—Size: Average size of the terminal leaflet is 30–35 mm (l)×18–22 mm(w). Shape: Elliptic to ovate. Margins: Finely serrated. Texture: Leathery.

Hips/seed formation: None observed.

Winter hardiness: Due to the variety's principal use in greenhouses, winter hardiness has not been evaluated.

Disease resistance: Average resistance to powdery mildew and *Botrytis* under normal growing conditions.

I claim:

1. A new and distinct variety of miniature rose plant characterized by the following combination of characteristics:

(a) forms abundant, attractive long lasting pink flowers;

(b) exhibits a compact and bushy growth habit;

(c) is suited for growing in greenhouse in pots from softwood cuttings, and;

(d) exhibits durable flowers and foliage suitable for distribution in the floral industry;

substantially as herein illustrated and described.

* * * * *

KORpagbel